United States Patent [19]

Komatsu et al.

[11] 4,450,111
[45] May 22, 1984

[54] PROCESS FOR THE PURIFICATION OF ANTHRAQUINONE

[75] Inventors: Tatsuyoshi Komatsu, Kamakura; Shigeaki Numata, Yokohama; Kazuhiro Maruyama, Kawasaki, all of Japan

[73] Assignee: Kawasaki Kasei Chemicals Ltd., Tokyo, Japan

[21] Appl. No.: 373,106

[22] Filed: Apr. 29, 1982

[30] Foreign Application Priority Data

Jun. 9, 1981 [JP] Japan ................................ 56-87499

[51] Int. Cl.³ .............................................. C07C 49/68
[52] U.S. Cl. ............................................... 260/369
[58] Field of Search .................................... 260/369

[56] References Cited

U.S. PATENT DOCUMENTS

| | | | |
|---|---|---|---|
| 1,404,056 | 1/1922 | Portheim | 260/369 |
| 2,120,678 | 3/1936 | Parsons et al. | 162/87 |
| 3,870,730 | 3/1975 | Scharte et al. | 260/369 |
| 4,155,922 | 5/1979 | Wenzel et al. | 260/369 |
| 4,284,576 | 8/1981 | Schenk et al. | 260/369 |

OTHER PUBLICATIONS

*Chemical Abstract*, vol. 82, No. 111821f, Paluch, "Reaction of Chlorine Dioxide and Sodium Chloride With Some Organic Compounds", 1974.
U. K. Search Report No. 13033 (1982).

*Primary Examiner*—Natalie Trousof
*Assistant Examiner*—Raymond Covington
*Attorney, Agent, or Firm*—Oblon, Fisher, Spivak, McClelland & Maier

[57] ABSTRACT

In a process for purifying crude anthraquinone obtained by the oxidation, by molecular oxygen in an aqueous alkali metal hydroxide solution, of an adduct obtained by the Diels-Alder reaction of butadiene with 1,4-naphthoquinone obtained by a catalytic vapor phase oxidation reaction of naphthalene, an improvement characterized in that said crude anthraquinone is subjected to oxidation treatment in an aqueous medium in the presence of a hypochlorite.

8 Claims, No Drawings

PROCESS FOR THE PURIFICATION OF ANTHRAQUINONE

BACKGROUND OF THE INVENTION

1. FIELD OF THE INVENTION

The present invention relates to a process for purifying crude anthraquinone (hereinafter referred to as "AQ") obtained by the oxidation, by molecular oxygen in the presence of a basic compound, of an adduct obtained by the Diels-Alder (hereinafter referred to as "DA") reaction of butadiene (hereinafter referred to as "BD") with 1,4-naphthoquinone (hereinafter referred to as "NQ") obtained by a catalytic vapor phase oxidation reaction of naphthalene.

2. DESCRIPTION OF THE PRIOR ART

AQ is an extremely important industrial material as an intermediate for dyestuffs. Recently, it has been found that AQ is useful also as a digesting assistant for pulps, and an attention has been drawn to its functions.

As a digesting assistant for pulps, AQ is desired to be inexpensive, available in fine particles and highly dispersible when added to water or white liquor.

As a popular method for the production of AQ, a so-called DA process is known in which an adduct obtained by the DA reaction of NQ with BD is oxidized in an aqueous medium in the presence of a basic compound. Crude AQ obtainable by this process is blackish brown and contains polycondensation products of NQ and by-products of the DA reaction, and it usually has a purity of not higher than 98%.

As an industrial method for the purification of the crude AQ, distillation is commonly used.

However, the melting point of AQ is extremely high at a level of 286° C. Accordingly, it is likely that polycondensation of the impurities and AQ proceeds during the melting or storage of the crude AQ or during the distillation, and the yield of refined AQ by the distillation will thereby be low. There are additional problems involved in the withdrawal of the residue, the recovery of AQ from the residue and the necessity of the treatment of the residue.

SUMMARY OF THE INVENTION

As a result of an extensive research with an aim to develop a method capable of readily purifying the crude AQ, the present inventors have found that if the crude AQ is treated in an aqueous medium in the presence of a hypochlorite, water-insoluble impurities which can not be removed by a usual warm water washing, can be made water-soluble and can thereby be removed, and it is thereby possible to improve the purity of the AQ. The refined AQ thereby obtained is yellow and presents a remarkably improved appearance. Thus, the present invention has been accomplished.

The present invention resides in a process for purifying crude AQ obtained by the oxidation, by molecular oxygen in an aqueous alkali metal hydroxide solution, of an adduct, i.e. 1,4,4a,9a-tetrahydroanthraquinone, obtained by the DA reaction of BD with NQ obtained by a catalytic vapor phase oxidation reaction of naphthalene, which process is characterized in that said crude AQ is subjected to oxidation treatment in an aqueous medium in the presence of a hypochlorite.

DETAILED DESCRIPTION OF THE PREFERRED EMBODIMENTS

As the NQ to be used in the process of the present invention, there may be mentioned, for example, the following NQs.

(1) NQ obtained by a method (Japanese patent publication No. 20026/78) in which NQ is extracted with use of a water-insoluble organic solvent (for example, an aromatic hydrocarbon such as ortho-xylene) from an aqueous slurry obtained by washing with water and collecting a reaction gas obtained by a catalytic vapor phase oxidation of naphthalene and comprising NQ and phthalic acid anhydride, and the phthalic acid is separated in a form of an aqueous solution.

(2) NQ obtained by a method (Japanese Laid-Open patent application No. 122246/79) on which NQ is extracted with use of a water-insoluble organic solvent from a wet cake composed of NQ and phthalic acid and obtained by filtering the above-mentioned aqueous slurry comprising NQ and phthalic acid.

(3) NQ obtained by a method (Japanese patent publication No. 14138/60) in which from a solution of NQ and phthalic acid anhydride obtained by collecting the reaction gas with an organic solvent having a high boiling point, only the phthalic acid anhydride is extracted in a form of phthalic acid with use of hot water.

(4) NQ obtained by a method (Japanese patent publication Nos. 29298/70 and 9209/78) in which a reaction gas obtained by oxidation of naphthalene is washed and collected with an aqueous solution of a mono-salt of phthalic acid or an aqueous medium, and a NQ slurry thereby obtained is filtered.

The DA reaction of NQ with BD is carried out by a known method, for example, usually in an organic solvent at a temperature of from 80° to 250° C. under pressure of from 1 to 30 kg/cm$^2$ for from 0.1 to 5 hours.

As a method for oxidizing the DA reaction adduct thereby obtained, by molecular oxygen to obtain crude AQ, there may be mentioned, for example, a method (Japanese patent publication No. 1267/78) in which the DA reaction adduct (i.e. 1,4,4a,9a-tetrahydroanthraquinone) is oxidized by air in an aqueous alkaline solution, and AQ crystals thereby formed are filtered and washed with water. The crude AQ thus obtained may be used in a form of a wet cake or, if necessary, in a form of a dried material.

As the oxidizing agent for the oxidation treatment of the crude AQ according to the present invention, a hypochlorite is used. By this oxidation treatment, the colour of the crude AQ is refined to yellow and the purity is raised by about 0.5 to 1% (according to the analysis of Japan Industrial Standards (JIS)).

It is rather surprising that when an ordinary oxidizing agent other than the hypochlorite, such as sodium chlorite, sodium chlorate, sodium perchlorate, a peroxide such as hydrogen peroxide, a peroxo acid salt such as sodium persulfate, nitric acid or iron chloride, is used instead of the hypochlorite, no adequate improvement of the colour is obtainable and no improvement in the purity of the AQ is obtainable by the treatment.

As the hypochlorite to be used in the present invention, there may be mentioned an alkali metal hypochlorite such as sodium or potassium hypochlorite, or a bleaching liquor (Ca(ClO)$_2$). However, sodium hypochlorite is preferably used. Instead of the oxidation treatment with sodium hypochlorite, it is possible to employ oxidation treatment wherein chlorine is blown into an aqueous sodium hydroxide solution.

In the present invention, the amount of the hypochlorite may vary depending upon the amount of the impurities in the crude AQ. However, the hypochlorite is used usually in an amount of from 0.5 to 30% by weight, preferably from 1 to 5% by weight based on the crude AQ. However, a greater amount may be used. In this case, it is possible to lower the treating temperature or to shorten the treating time.

The process of the present invention can be conducted generally in the following manner. Namely, NQ obtained by a catalytic vapor phase oxidation reaction of naphthalene and BD are subjected to the DA reaction in a solvent such as othoxylene, and the reaction solution thereby obtained is contacted with an aqueous sodium hydroxide solution to extract the DA reaction adduct as a sodium salt in the aqueous phase. The aqueous solution thus obtained is contacted with air in the presence or absence of an aromatic hydrocarbon to effect the oxidation reaction. After completion of the reaction, the crystallized AQ is filtered and washed with water. The crude AQ wet cake thus obtained is converted into a slurry by an addition of water, and a predetermined amount of a hypochlorite is added to the slurry, and the mixture is subjected to oxidation treatment at a predetermined temperature under stirring. After the treatment, the slurry is filtered and washed with water, and, if necessary, the remaining hypochlorite ions are decomposed with use of a reducing agent such as a thiosulfate or hydrogen peroxide, and the substance thereby obtained is dried to obtain refined yellow AQ.

In the above treatment, the concentration of the aqueous slurry of the crude AQ may be at any level so long as the slurry is flowable. However, the concentration is usually preferred to be within a range of from 10 to 30% by weight, more preferably from 15 to 30% by weight. The concentration of the hypochlorite is usually from 0.1 to 3% by weight, preferably from 0.3 to 2% by weight. The treating temperature may be within a range of from 30° to 100° C. However, with a view to avoidance of corrosion of the treating vessel, the temperature is preferably within a range of from 40° to 80° C. The treating time is from 0.25 to 4 hours, preferably from 0.5 to 2 hours.

The AQ thus obtained by the process of the present invention has an extremely small particle size, and thus has considerably better dispersibility in water than finely pulverized AQ refined by distillation. It is particularly advantageous when used as a digesting assistant for pulps. As a digesting assistant for pulps, it may be used in a form of a wet cake or a dried product. However, it is preferred that the AQ has a water content of 30% (wet standards), whereby it is adequately dispersible in water or white liquor even in the absence of a surfactant.

The present invention makes it possible to attain a high yield of at least 99% as compared with the conventional purification process by distillation, with a simple apparatus, and thus provides an extremely valuable industrial process whereby fine yellow AQ powder having a purity of at least 98% can readily be prepared.

Now, the present invention will be described more specifically with reference to Examples. However, it should be understood that the present invention is not limited to these Examples. In the Examples, "part(s)" and "%" are meant for "part(s) by weight" and "% by weight," respectively.

EXAMPLE 1

An aqueous slurry obtained by washing with water and collecting a reaction gas formed by a catalytic air oxidation reaction of naphthalene, was extracted with orthoxylene, and the NQ-orthoxylene solution thereby obtained was subjected to the DA reaction. Then, the DA reaction adduct was extracted with an aqueous sodium hydroxide solution, and air was introduced into the aqueous solution to form AQ. The slurry thereby obtained was filtered and washed with water, whereupon a wet cake of crude AQ (water content: 50%, purity: 97.5%) was obtained. 120 parts of the cake and 180 parts of water were introduced in a glass reactor having a capacity of 500 parts by volume, and 10 parts of an aqueous solution containing 14% of sodium hypochlorite was added. The mixture was subjected to oxidation treatment at 60° C. for one hour under stirring. The slurry thus obtained was filtered under suction by means of a Nutsche funnel, washed on the funnel with 80 parts of warm water, and dried to obtain 59.3 parts of yellow crystal powder.

The purity was analyzed in accordance with the purity measuring method stipulated by "JIS K 4145." The purity was thereby found to be 98.5%. The yield of the refined AQ based on the AQ content in the crude AQ was about 100%.

Comparative Example 1

120 parts of the wet cake of crude AQ used in Example 1 and 180 parts of water were introduced in a glass reactor having a capacity of 500 parts by volume, and subjected to treatment in the same manner as in Example 1 except that sodium hypochlorite was not added, whereupon dark brown crystal powder was obtained. The amount of the AQ thereby obtained was 59.7 parts, and the purity was 97.5%.

Comparative Example 2

Oxidation treatment was conducted in the same manner as in Example 1 except that instead of sodium hypochlorite, various oxidizing agents were used in the same molar ratio. The results thereby obtained are shown in the following Table.

| Oxidizing agents | Purity (%) | Colour*1 |
|---|---|---|
| None | 97.6 | X |
| $NaClO_2$ | 97.4 | Δ |
| $NaClO_3$ | 97.3 | X |
| $NaClO_4$ | 97.6 | X |
| $H_2O_2$ | 97.7 | X |
| $CH_2COOOH$ | 97.9 | ◎ |
| $Na_2S_2O_8$ | 97.6 | Δ |
| $HNO_3$ | 97.6 | Δ |
| $FeCl_3$ | 96.4 | Δ |
| $HClO_4$ | 97.4 | Δ |

*1 ◎ Remarkably improved
○ Fairly improved
Δ Slightly improved
X No improvement

EXAMPLE 2

100 parts of a wet cake of crude AQ (water content: 45%, purity: 97.8%) obtained by the DA process in a manner similar to Example 1 and 50 parts of water were introduced in a glass reactor, and 10 parts of an aqueous solution containing 14% of sodium hypochlorite was added. The mixture was heated at 50° C. for 2 hours under stirring. The slurry thereby obtained was centrifuged to separate AQ crystals, and the wet cake thereby obtained was made into a 20% slurry by an addition of water. Then, about 7.5 parts of an aqueous solution containing 5% of sodium thiosulfate was added under stirring to reduce effective chlorine. The slurry thereby obtained was filtered by a centrifugal dehydrating apparatus.

The wet cake thereby obtained had extremely good dispersibility in water, and then dispersed in water, gave a stable slurry.

The yield of the refined AQ was about 100%, and the purity was 98.7%.

We claim:

1. In a process for purifying crude anthraquinone obtained by the oxidation of the adduct obtained from the Diels-Alder reaction of butadiene with 1,4-naphthoquinone, said naphthoquinone being obtained by the catalytic vapor phase oxidation of naphthalene with molecular oxygen in an aqueous alkali metal hydroxide solution, the improvement comprising:

subjecting said crude anthraquinone to oxidation in an aqueous medium containing hypochlorite ion as the sole oxidizing agent.

2. The process according to claim 1 wherein said hypochlorite is sodium hypochlorite.

3. The process according to claim 1 wherein said hypochlorite is present in an amount of from 0.5 to 30% by weight based on the crude anthraquinone.

4. The process according to claim 1 wherein said crude anthraquinone is in a form of an aqueous slurry containing from 10 to 30% by weight of anthraquinone and the concentration of the hypochlorite is from 0.1 to 3% by weight.

5. The process according to claim 4 wherein the temperature for the oxidation treatment is from 30° to 100° C.

6. The process according to claims 1, 2, 3 4, or 5 wherein the oxidation treatment is carried out from 0.25 to 4 hours.

7. The process according to claim 1 wherein said crude anthraquinone is in a form of an aqueous slurry containing from 15 to 30% by weight of anthraquinone and the concentration of the hypochlorite is from 0.3 to 2% by weight.

8. The process according to claim 1 or 7 wherein the temperature for the oxidation treatment is from 40° to 80° C.

* * * * *